(12) United States Patent
Steenbergen (10) Patent No.: US 9,357,962 B2
(45) Date of Patent: Jun. 7, 2016

(54) DEVICE AND METHOD FOR PHOTON ABSORPTION COEFFICIENT MEASUREMENT

(75) Inventor: Wiendelt Steenbergen, Enschede (NL)

(73) Assignee: Universiteit Twente, Enschede (NL)

( * ) Notice: Subject to any disclaimer, the term of this patent is extended or adjusted under 35 U.S.C. 154(b) by 912 days.

(21) Appl. No.: 13/321,511

(22) PCT Filed: May 26, 2010

(86) PCT No.: PCT/EP2010/057258
§ 371 (c)(1),
(2), (4) Date: Jan. 26, 2012

(87) PCT Pub. No.: WO2010/142530
PCT Pub. Date: Dec. 16, 2010

(65) Prior Publication Data

US 2012/0116204 A1 May 10, 2012

(30) Foreign Application Priority Data

Jun. 10, 2009 (EP) .................................... 09162394

(51) Int. Cl.
*A61B 5/05* (2006.01)
*A61B 5/00* (2006.01)
*A61B 8/08* (2006.01)

(52) U.S. Cl.
CPC ............... *A61B 5/415* (2013.01); *A61B 5/0095* (2013.01); *A61B 5/0097* (2013.01); *A61B 5/418* (2013.01); *A61B 5/4312* (2013.01); *A61B 8/0825* (2013.01)

(58) Field of Classification Search
None
See application file for complete search history.

(56) References Cited

U.S. PATENT DOCUMENTS

2005/0004458 A1* 1/2005 Kanayama et al. ........... 600/437
2005/0256403 A1 11/2005 Fomitchov et al.
(Continued)

FOREIGN PATENT DOCUMENTS

EP 1008326 6/2000
EP 1493380 1/2005
(Continued)

OTHER PUBLICATIONS

Steenbergen, Wiendelt, "Photoacoustic Cancer Imaging", Acoustics 2008, Paris, FR, abstract from J. Acoust. Soc. Am., vol. 123, No. 5, Pt. 2, May 2008, p. 3369.*
(Continued)

*Primary Examiner* — Christopher Cook
(74) *Attorney, Agent, or Firm* — Bret E. Field; Bozicevic, Field & Francis LLP (57) ABSTRACT

The invention relates to a method and a device, suitable for the measurement of quantitative photon absorption coefficient in tissue, wherein the device comprises a first light source, suitable for generating photons, a light measurement element suitable for measuring at least one of: the intensity, the frequency, the frequency deviations and phase shift of the light to be measured, an ultrasound source, suitable for the generation of a defined sound wave pattern in a defined volume element within the tissue, wherein the ultrasound source is suitable for labelling the light, originating from the first light source or a second light source that enters the defined volume element within the tissue, and an ultrasound measurement element, suitable for measuring ultrasound, originating from the defined volume element within the tissue and generated by the light of the first light source that enters the defined volume element within the tissue.

16 Claims, 3 Drawing Sheets

(56) References Cited

U.S. PATENT DOCUMENTS

| | | |
|---|---|---|
| 2006/0058685 A1* | 3/2006 | Fomitchov et al. ........... 600/476 |
| 2007/0093708 A1 | 4/2007 | Benaron et al. |
| 2008/0077002 A1 | 3/2008 | Nielsen et al. |
| 2009/0198128 A1* | 8/2009 | Fukutani et al. ............. 600/437 |
| 2011/0190617 A1* | 8/2011 | Chen ............................ 600/407 |

FOREIGN PATENT DOCUMENTS

| | | |
|---|---|---|
| EP | 2036488 | 3/2009 |
| EP | 2036490 | 3/2009 |

OTHER PUBLICATIONS

Wang et al. "Tomographic imaging of absolute optical absorption coefficient in turbid media using combined photoacoustic and diffusing light measurements", Optics Letters, vol. 32, No. 17, Sep. 1, 2007.*

Wang, Lihong, V., "Ultrasound-mediated biophotonic imaging: A review of acousto-optical tomography and photo-acoustic tomography", Disease Markers, 19, 2003, pp. 123-138.*

* cited by examiner

DEVICE AND METHOD FOR PHOTON ABSORPTION COEFFICIENT MEASUREMENT

The invention relates to a device and a method for photon absorption coefficient measurement. More specific, the invention relates to the calculative deduction of photon absorption coefficient in a defined volume element by measuring the amount of sound generated within the defined volume element when irradiated with a defined light pulse.

In the art, this technique is referred to as photo acoustic or opto acoustic measurement. When the specific photon absorption coefficient of a number of defined volumes is deduced, a graphic representation of the specific photon absorption coefficient of a portion of material or tissue can be generated. This technique is referred to as photo acoustic or opto acoustic imaging.

Devices used to perform this technique can be applied in e.g. two or three dimensional imaging of materials, constructions, for instance in non destructive testing applications, of food and of tissues like e.g. in vivo tissues.

In the art, a pulsed or modulated light source irradiates specific areas of a tissue sample, and an array of ultrasonic transducers measures sound pressure waves, generated within the tissue sample by the pulsed light. From the data obtained with the array of pressure transducers, through appropriate processing of the data, a quantitative photo acoustic image of the tissue sample can be generated. This technique is for instance described in the international application WO2007/084771.

However, due to the phenomenon of light scattering, the photo acoustic methods and devices in the art suffer from the fundamental inability to quantify photon absorption coefficients and/or chromophore concentrations within a tissue in absolute terms.

Accordingly it is an object of the invention to mitigate or solve these above described and/or other problems of devices and methods for photo acoustical imaging in the art, while maintaining and/or improving the advantages thereof.

This and/or other objects are reached by a device, suitable for the measurement of quantitative photon absorption coefficient in tissue, wherein the device comprises a first light source, suitable for generating photons, a light measurement element suitable for measuring at least one of: the intensity, the frequency, the frequency deviations and phase shift of the light to be measured, an ultrasound source, suitable for the generation of a defined sound wave pattern in a defined volume element within the tissue, wherein the ultrasound source is suitable for labelling the light, originating from the first light source or from a second light source that enters the defined volume element within the tissue, and an ultrasound measurement element, suitable for measuring ultrasound, originating from the defined volume element within the tissue and generated by the light that enters the defined volume element within the tissue.

The above described and/or other objects are similarly reached by a method suitable for the measurement of quantitative photon absorption coefficient in tissue, wherein a device as described above is provided, wherein a defined sound wave pattern is generated in a defined volume element within the tissue to be examined, wherein the tissue to be examined is irradiated with the first and the second light source, wherein the light that enters the defined volume is labelled by means of the defined sound wave pattern in the defined volume element, wherein the amount of labelled light exiting the tissue is measured, wherein the amount of light originating from the first light source that actually entered the defined volume element is calculated, wherein the amount of sound generated within the tissue at the tissue surface is measured at the tissue surface, from which the amount of sound generated in the defined volume element is calculated wherein the amount of photon absorption coefficient of the defined volume element within the tissue is deduced from the calculated amount of light that originates from the first light source and that entered the defined volume element and from the amount of sound generated in the defined volume element.

By labelling the light that originates from a defined volume element, the measured light intensity can be corrected for the non labelled light. Thus a far more exact flux of light trough the defined volume element can be calculated.

From the dose of light the defined volume element is experiencing and the generated acoustical pattern, a specific photon absorption coefficient can be calculated. Thus if the dose of light, the defined volume is experiencing, is more precisely known, a far more accurate specific photon absorption coefficient of the defined volume can be calculated. By this more precisely known specific photon absorption coefficient of a number of defined volumes within a tissue, a quantative image can be generated of the photon absorption coefficient.

Accordingly, the embodiments described in current disclosure provide a breakthrough in the quantification problem in photo acoustic technology. The essential steps towards truly quantitative functional and molecular imaging for diagnosis of major diseases such as breast cancer are thus provided.

A further advantage is that this quantification relies on a minimum of numerical and/or computational models for the light propagation through tissue. The ability to quantify thus has become an inherent property of the technique.

A further aspect of the invention is that the light source is a laser and the laser is preferably configured to dose the light in a pulsed way. By applying laser light, a well defined generally in phase source is provided, of which the labelled portion by means of the acousto-optical labelling, as is described hereinbefore, can be readily detected.

Due to the application of a pulse or a set of pulses of well defined light, a properly defined sound pressure wave can be generated, which is clear and more practically detectable.

Another aspect of the disclosure is that the device is provided with a processor, which is at least in communicative contact with the light measurement element and the ultrasound measurement element. By means of this processor, from the input data such as the amount of light applied, the amount of light measured, the amount of acoustic energy applied and the amount of acoustic energy measured, the specific photon absorption of the volume element can be calculated. Herein the processor can be configured to deduce from the information provided by the light measurement element which portion of the light originates from the defined volume element.

More specific, the processor can be configured to deduce from the amount of light generated by the light source, and from the amount of light originating from the defined volume element, an amount of light actually entering the defined volume element. The processor can be further configured to deduce from the measured sound, generated in the defined volume within the tissue, and the amount of light actually entered the defined volume within the tissue, a specific photon absorption coefficient of the defined volume within the tissue.

In another aspect of the current disclosure, the device can be configured to scan through at least a portion of the tissue by measuring consecutive defined volumes within the tissue, deducing the respective specific photon absorption coefficient of each of the defined volumes and wherein the device is further configured to generate from the thus generated data a graphic representation of the tissue, wherein different regions with different specific absorption coefficients are configured to be visually determinable. By generating such a graphic representation, different regions can be visualised. Thus an examination of the tissue in question can reveal aberrations of the photon absorption coefficient within the tissue and thus be a powerful aid in diagnosis.

Another aspect of the current disclosure is that the light source and/or the ultrasound source, can comprise arrays or matrices of individual sources and the ultrasound measuring element and/or the light measuring element comprises arrays or matrices of individual measuring sensors.

By the application of arrays, statistical calculations can be performed to more accurately determine the light exposure of the tissue and/or the origin of the generated pressure waves. By applying arrays, more simultaneous measurements can be performed.

In order to further elucidate the invention, exemplary embodiments will be described with reference to the drawing. In the drawing.

The figure represents a specific exemplary embodiment of the inventions and should not be considered limiting the invention in any way or form. In the figure the same or corresponding reference numerals are used for the same or corresponding elements.

Throughout the description and the claims the expression "fluence" is to be understood as, though not to be considered limited to the normally applied radiometric quantity fluence, being the total amount of optical energy deposited at a point inside the tissue per unit of area.

The expression "dose" is to be understood though not to be considered limited to the total amount of optical energy at a defined volume element within the tissue.

The expression "specific or quantitative photon absorption" is to be understood as, though not to be considered limited to the ratio of the amount of volumetrically absorbed photons and the total dose of photons.

The expression "labelling" is to be understood as, though not to be considered limited to superpose or to overlay a specific frequency and/or modulation to a portion of an electromagnetic wave such as a light wave such that it can be recognised and distinguished from other light, eventually originating from the same light source that is not thus labelled.

One of the fields of application of the device and the method according to the invention is to spot abnormal tissue within normal in vivo tissue. These abnormal tissues such as cancer tissue or chronically damaged tissue, often differ in photon absorption coefficient from healthy tissues.

Photo acoustic imaging (PA) is a relative novel technique for studying tissue abnormalities based on their deviating optical absorption coefficient from normal tissue. This technique is based on a physical principle that light is absorbed in the tissue structure. This absorption generates a local increase in temperature, which locally and relative rapidly alters the local specific density. This sudden increment of the density, and thus a local expansion of the tissue material will generate a measurable sound wave within the tissue.

The photon absorption is dependent on the specific properties of the tissue in question, and when e.g. red light is used, for instance tissues with a relative high amount of blood will exhibit a strong absorption, generating a relative strong acoustic wave. On the other hand tissues with little blood will have a relative low absorption, and thus a relative modest volumetric expansion, generating only a modest sound wave.

Besides the relative absorption of the tissue in question, also other specific physical properties of the tissue in question can alter the intensity of the sound thus generated. For example the specific elasticity, the specific thermal expansion, the specific heat capacity of the tissue in question can influence the generated acoustic intensity.

In photo acoustics, the photon absorption of short light pulses thus generates thermo elastic stresses which lead to the emission of ultrasound waves. These enable imaging of absorbing substances in turbid media in three dimensions, with a high spatial resolution.

An absolute quantification of the specific photon absorption coefficients and/or chromophore concentrations within the tissues requires that the local fluence of excitation light inside the tissue is known. From the local fluence within a defined volume and the measured sound generated, the specific photon absorption can be calculated.

In current application it is proposed to deduce the local fluence of a defined volume element by the application of a locally well defined, focused ultrasound wave field. The focus of the ultrasound wave field can coincide with the defined volume and can actually define the volume element as such.

Light crossing the defined volume element of the ultrasound focus will be phase-modulated through sound-driven refractive index variations and motion of scattering centres. Thus the specific light passing through the defined volume element becomes labelled and identifiable. The light which is thus labelled by the so called acousto-optic (AO) effect can for instance be detected by means of interferometric methods. By applying an defined volume ultrasound wave field focus, the local absorption coefficients can be calculated based on combined photo acoustic and acousto-optic measurements using e.g. specific locations of injection and detection of light.

In the measurement techniques as described in the current disclosure, an important underlying property is that light can travel any path through a scattering medium in two directions with equal probability. This means that the probability that a single photon will reach through a turbid medium over a specific distance from one side to the other is equal to the probability that a photon will reach through the same specific distance in reversed direction. Why this phenomenon is considered relevant, is further elucidated hereinafter.

Malignant tumors are often characterised by increased haemoglobin content and lower partial oxygen pressure, when compared to healthy tissue. Imaging these quantities based on their absorption contrast may improve the diagnosis of various types of soft tissue cancers. Also other abnormalities or disease-relevant tissues can be observed by their absorption contrast, either with or without the application of a contrast agent. Examples are locations of chronic tissue damage which are often characterised by hypoxia, or sentinel lymph nodes which are visualised with optical dyes.

Photo acoustics is a relative new imaging modality whose properties makes it a good candidate for providing such data with high imaging depth and high resolution. When for example breast tissue of a patient with breast cancer, is irradiated with a light source having a wavelength of 1064 nm, a reconstructed distribution of optical absorption of a thin slice of breast tissue containing the tumor can clearly visualise the location and size of the tumor in question, even at a depth of beyond 1 cm.

The breast tumor can show enhanced absorption in contrast to the normal breast tissue, due to the large concentration of haemoglobin compared to the adjacent normal breast tissue. Such images can for instance be generated with a photo acoustic mammoscope as presented and described in: Manohar, S., et al., "Initial results of in vivo non-invasive cancer imaging in the human breast using near infrared photo acoustics", Optics Express, 2007 15(19), p. 12277-12285.

At best, such images display the spatial distribution of the amount of locally absorbed energy per unit volume. However, this amount of the locally absorbed energy depends on both the local photon absorption coefficient and the locally available amount of light.

In the state of the art of photo acoustic imaging, these quantities cannot be separately measured, which fundamentally prevents a proper deduction or calculation of the value of the specific photon absorption coefficient in a defined volume within the tissue and thus prevents a quantification of for instance chromophores such as (oxy)haemoglobin in said volume.

For these reasons a proper graphic representation of the specific photon absorption coefficient, which can clearly visualise the locally present amount of chromophores is, up to now, not possible.

Thus a need exists for measurement of the local concentration of chromophores in living tissue in absolute units. Preferably, these concentrations can be graphically represented in absolute terms, and in three dimensions. In order to do so, this quantification requires three-dimensional data of the locally present photon absorption coefficient.

The graphic representation of the absolute concentration of chromophores in biological tissues can be performed by an ingenious combination of two types of interplay of light and sound. A first interplay is known as photo acoustics (PA), in which ultrasound waves are generated through thermo-elastic generation using short light pulses or a rapidly modulated light source, as described above. A second interplay is the effect of acousto-optics (AO), wherein the acousto-optic labelling of photons is performed by using focused ultrasound.

Figure 1:
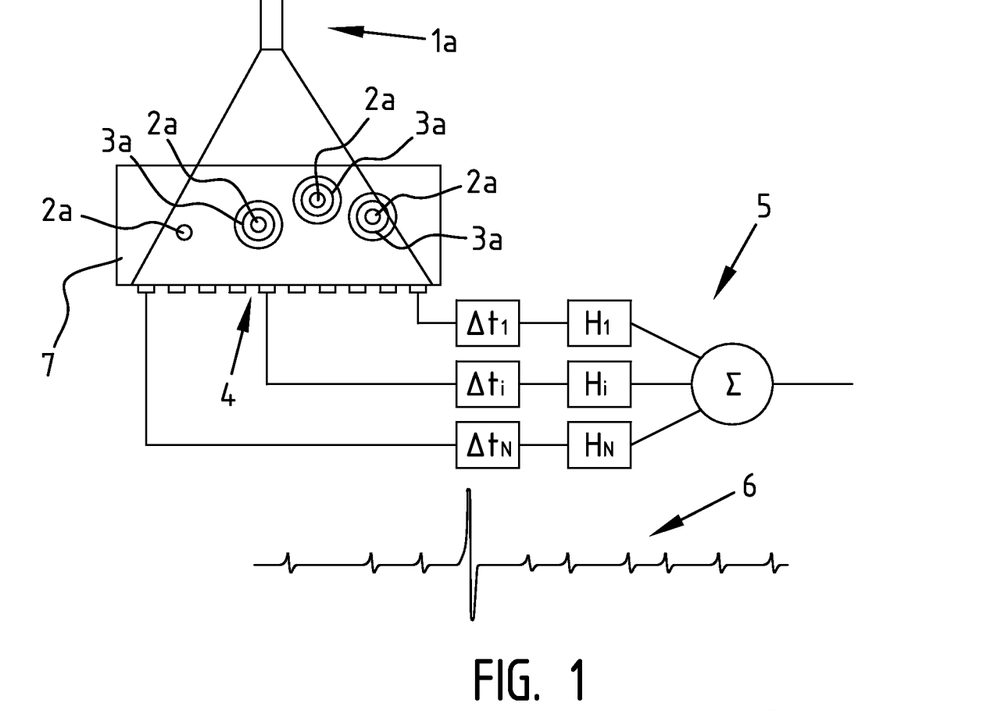
FIG. 1 represents a schematic view on a tissue sample, wherein a device and method according to the state of the art is applied.

In FIG. 1, a schematic representation of the photo acoustical imaging as performed in the art is shown. Photoacoustic imaging (PAI) is based on the thermo-elastic generation of acoustic waves by absorption of pulsed or modulated light. The absorption of short light pulses such as e.g. nanosecond pulses 1 can cause a small local rise of the temperature of absorbing elements 2 within the turbid medium such as a tissue 7. This results in restricted dilatation of the absorbing tissue, leading to local stresses. These internal stresses can relax by the emission of ultrasound waves 3, represented in FIG. 1 as concentric circles. The origin of the ultrasound waves can be reconstructed in three dimensions when the time evolving ultrasound pressure wave $p_i(t)$ is measured at a sufficient number of discrete locations i on the surface 4 of the turbid medium 7. One of the various source location reconstruction methods (although not the most quantitative one) is e.g. the delay-and-sum algorithm, which retrieves the photoacoustic source strength at a specific location inside the tissue by applying a proper time delay on all detected signals and adding them as is represented in FIG. 1 by function box 5.

Besides the delay-and-sum algorithm also more quantitative methods of image reconstruction for reflection mode signals have been developed, such as e.g. the Fourier-domain algorithm. Another proper reconstruction of the initial pressure distribution can be obtained with tomographic back projection algorithms, which require data acquisition along a closed contour or surface around the object.

PAI has successfully been applied to in vivo imaging of blood vessels both in small animals and humans. In phantoms an imaging depth of 30-35 mm could be achieved while in clinical experiments of photo-acoustic mammography depths of 18 mm could be reached. With further technological sophistication as provided by this disclosure, photo-acoustic imaging of deeply embedded chromophores can be made feasible within seconds to a few minutes. The outstanding virtue of photo-acoustic imaging is that it combines the high contrast offered by optical absorption of biological chromophores with the large transparency of tissue to ultrasound on the other hand. Unlike purely optical methods, the resolution of photo-acoustic imaging is not deteriorated by light scattering.

If a sufficiently short light pulse is applied to tissue, the photo-elastically generated initial local pressure $p_0$, directly after the pulse, before the onset of stress relaxation, will read:

$$p_0 = \Gamma \Phi c \epsilon_a = \Gamma \Phi \mu_a \qquad (1)$$

with $\Gamma$ the Grueneisen coefficient, $\Phi$ the local light fluence, c the concentration of the chromophore, $\epsilon_a$ the chromophore's molar optical absorption coefficient and $\mu_a$ the total local absorption coefficient. From the ultrasonic pressure waves $p_i(t)$ measured at the tissue surface the initial pressure distribution $p_0$ inside the tissue can be reconstructed. However, this determination of absolute chromophore concentrations is hampered by the fact that the local fluence $\Phi$ inside the tissue, which gives the optical energy that locally excites the chromophore, is unknown. This quantification problem and the way of solving it according to the invention are described hereinafter.

Thus, the dependence of the initial pressure $p_0(x,y,z)$ on both the unknown absorption coefficient $\mu_a(x,y,z)$ and the unknown spatial distribution of the optical fluence $\Phi(x,y,z)$ will hereinafter be solved.

Figure 2:
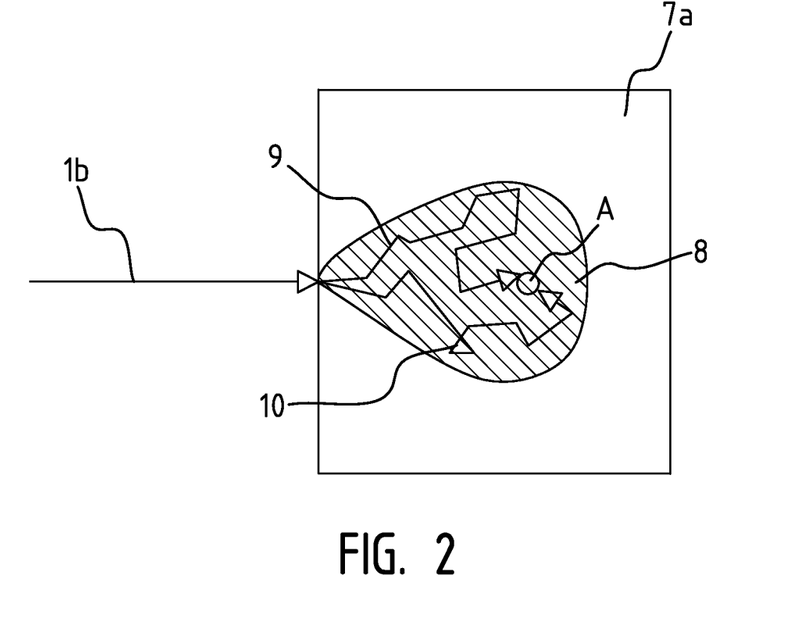
FIG. 2 represents a schematic sectional view of a portion of tissue to be examined in which scattering effects are depicted.

The local fluence at a certain point A (see FIG. 2) inside a scattering medium 7a such as a tissue 7 depends on the scattering and absorption properties in all parts of the medium 7a that have been addressed by the photons before they reached point A. Hence, the initial pressure $p_0$ generated in point A will depend in a nonlinear manner on the absorption and scattering properties in the entire shaded region 8, as is depicted in FIG. 2. In this figure the initial pulse 1b, is scattered in individual photon paths as is schematically visualised by the photon paths 9 and 10, which finally reach the point A.

Other obstacles in finding the local photon absorption coefficient are the challenges in reconstructing initial pressure $p_0$ and spatial variations in Grueneisen coefficient $\Gamma$. A first estimate can be that the latter is constant in the tissue to be examined. Though this is not correct, for first estimation reasons, this generalisation can be made without considerable loss in accurate calculation of photon absorption coefficients.

As mentioned before, another obstacle in finding the local photon absorption coefficient is the scattering coefficient. This phenomena renders it extremely difficult to calculate the local fluence throughout the tissue to be examined.

In the art several attempts have been proposed to model the scattering coefficient by applying correction methods, based on modelling light transport. A first approach can be that the tissue to be examined has a homogeneous scattering. Further models apply statistical algorithms to model the spatially varying scattering properties of the tissue to be examined. So a calculative quantification of the fluence remains, even with sophisticated algorithms, relatively poor.

Figure 3:
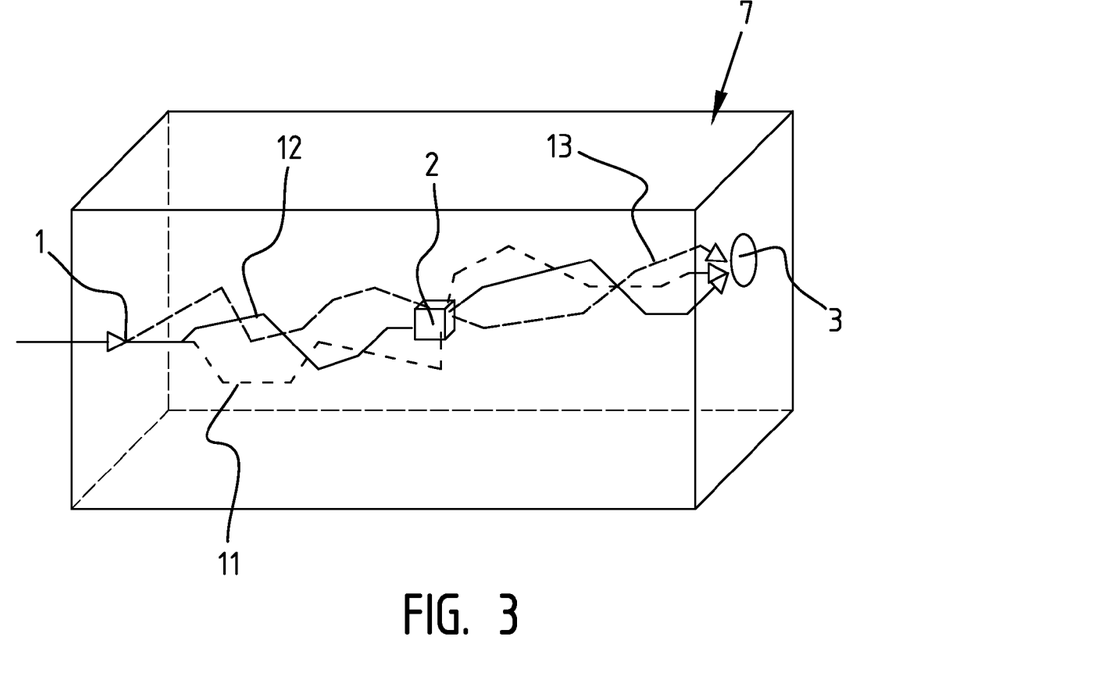
FIG. 3 represents a schematic three dimensional view on a portion of tissue to be examined, with schematically drawn possible photon trajectories.

In the invention, the fluence through a defined volume element is no longer calculated, but instead, measured by labelling light by means of an ultrasound focus. In FIG. 3 an example is given of a few photon trajectories 11, 12, 13 of the many photon trajectories between the injection point at position 1, via the defined volume element 2 inside the medium 7, to detection window at position 3.

Each of the many photon paths from position 1, via the defined volume element 2, to position 3, can be travelled in the reverse direction with the same probability Pr(1,2,3), provided that internal specular reflection is negligible, and provided that the scattering phase functions are independent of the direction of incidence of photons.

The probability that a photon travels along any path from position 1 to the defined volume element 2, or from position 1 to position 3 via defined volume element 2, is denoted by Pr(1,2) and Pr(1,2,3) respectively. Furthermore, the fluence in the defined volume element 2 of photons injected at position 1 is denoted by $\Phi_{12}$. Since this fluence $\Phi_{12}$ depends on the probability that photons reach the defined volume element 2 following any trajectory 11, 12 or 13, it is reasonable to assume that $\Phi_{12} \propto Pr(1,2)$. Equivalent considerations hold if photons are injected at position 3. Hence we can write:

$$\Phi_{12} \propto Pr(1,2) \text{ and } \Phi_{32} \propto Pr(3,2) \quad (2)$$

Of the photons arriving in volume element 2, some will be absorbed in the volume element 2. This probability of absorption in volume element 2 with photon injection at position 1 or 3 can be estimated from the reconstructed pressures $p_{12}$ and $p_{32}$ respectively, which read:

$$p_{12} = \Gamma \mu_{a,2} \Phi_{12} \text{ and } p_{32} = \mu_{a,2} \Phi_{32} \quad (3)$$

Other photons will not be absorbed in the defined volume element 2 and arrive at position 3. If volume element 2 is taken sufficiently small, survival is more likely than absorption. Suppose that photons addressing the defined volume element 2 obtain a label through which they can be recognised at position 3, the power $P_{L,13}$ of labelled photons detected at position 3 after injection at position 1 can be written as:

$$P_{L,13} \propto (Pr(1,2,3) \propto Pr(1,2)Pr(2,3) \propto (Pr(1,2)Pr(3,2)) \quad (4)$$

Wherein the last step can be justified by the reversibility principle. The second step, stating that: $Pr(1,2,3) \propto Pr(1,2)Pr(2,3)$, appears to be a simplification, though it can be justified by the reasoning that the probability of a photon to reach the detection window at position 3 by a trajectory going through the defined volume element 2, can be equal to the multiplication of the probability that a photon reached from the injection at position 1 the defined volume element 2 and the probability that a photon reaches from the defined volume element 2 to the detection window at position 3. The smaller the defined volume element 2 is chosen, the more accurate this simplification will be.

Substitution of equations (2) in equation (4) gives:

$$P_{L,13} \propto \Phi_{12} \Phi_{32} \quad (5)$$

A combination of equations (3) and equation (5) leads to the final result:

$$\mu_{a,2} = cSQRT(p_{12}p_{32}/P_{L,13}) \quad (6)$$

In this equation, the constant c will depend on Grueneisen parameter $\Gamma$ and instrumental details such as the size of the labelling volume, being the defined volume element 2 and optical detection apertures. Equation (6) suggests that it is possible to estimate the local absorption coefficient purely by external probing. This involves 1. A photo-acoustic excitation with pulsed light at positions 1 and 3 respectively and reconstruction of the resulting initial thermo-elastic stresses $p_{12}$ and $p_{32}$ in volume 2.

2. A detection in position 3 of light injected in position 1, and labelled in the defined volume element 2 by focussed ultrasound.

3. The application of equation (3) leads to an estimation of the fluences $\Phi_{12}$ and $\Phi_{32}$.

Alternatively, if the injection position 1 and the detection position 3 for the detection of the labelled light coincide, equation (5) directly leads to $\Phi_{12} \propto SQRT(P_{L,11})$ without using the photo-acoustic pressures. This suggests that the fluence rate can be determined with reflection mode acousto-optics only. This gives an outlook on wider applicability for all optical methods whose quantitative power is now limited due to unknown fluences. An example is molecular imaging using fluorescent molecular probes. However, with pure reflection mode acousto-optics the labelled light will be overwhelmed by non-labelled light, leading to a high noise level.

Figure 4:
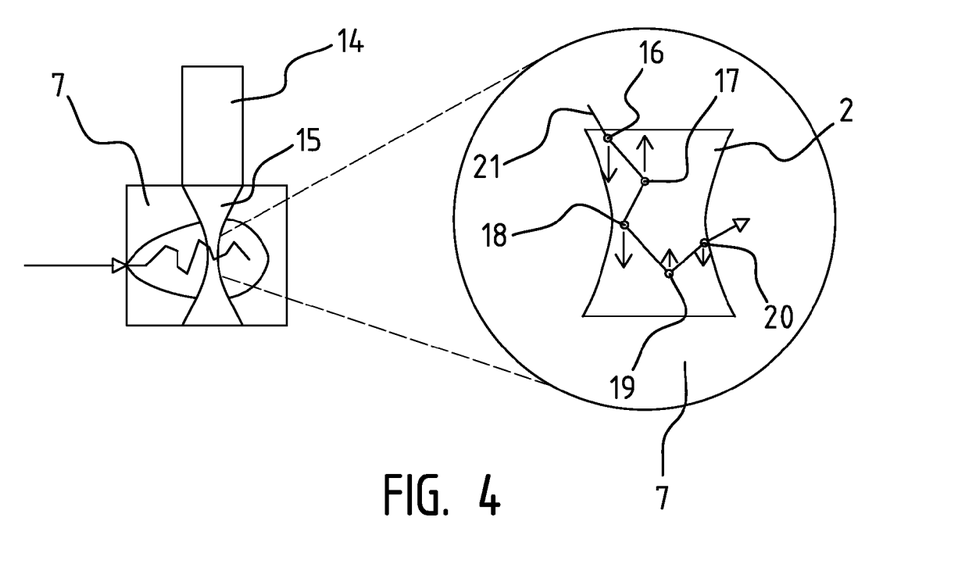
FIG. 4 represents a schematic representation of an acoustic labelling of light.

In FIG. 4, a schematic representation of a technique is depicted for specifically labelling photons that pass through a defined volume 2 within the tissue. In this embodiment, the photons are labelled by means of focused ultrasound. In FIG. 4, an ultrasound source 14 is provided in close proximity of the tissue 7 to be examined. The ultrasound source 14 is suitable for generating a focussed wave pattern 15 which defines a volume element 2. The local application of ultrasound (US) has two effects which can be optically detected:

1) scattering centres 16-20 in the turbid medium, being the tissue 7 to be examined are mechanically displaced by the US wave 15;

2) the refractive index is modulated by the density variations imposed by the US wave 15 (piëzo-optic effect).

Both mechanisms lead to a modulation of the optical path length 21 of photons which have crossed the ultrasound focus 15 coinciding with the defined volume element 2: the ultrasound thus has 'tagged' or 'labelled' these photons. Spatial resolution of the labelling can be obtained by using ultrasound pulses with a duration of microseconds.

Figure 5:
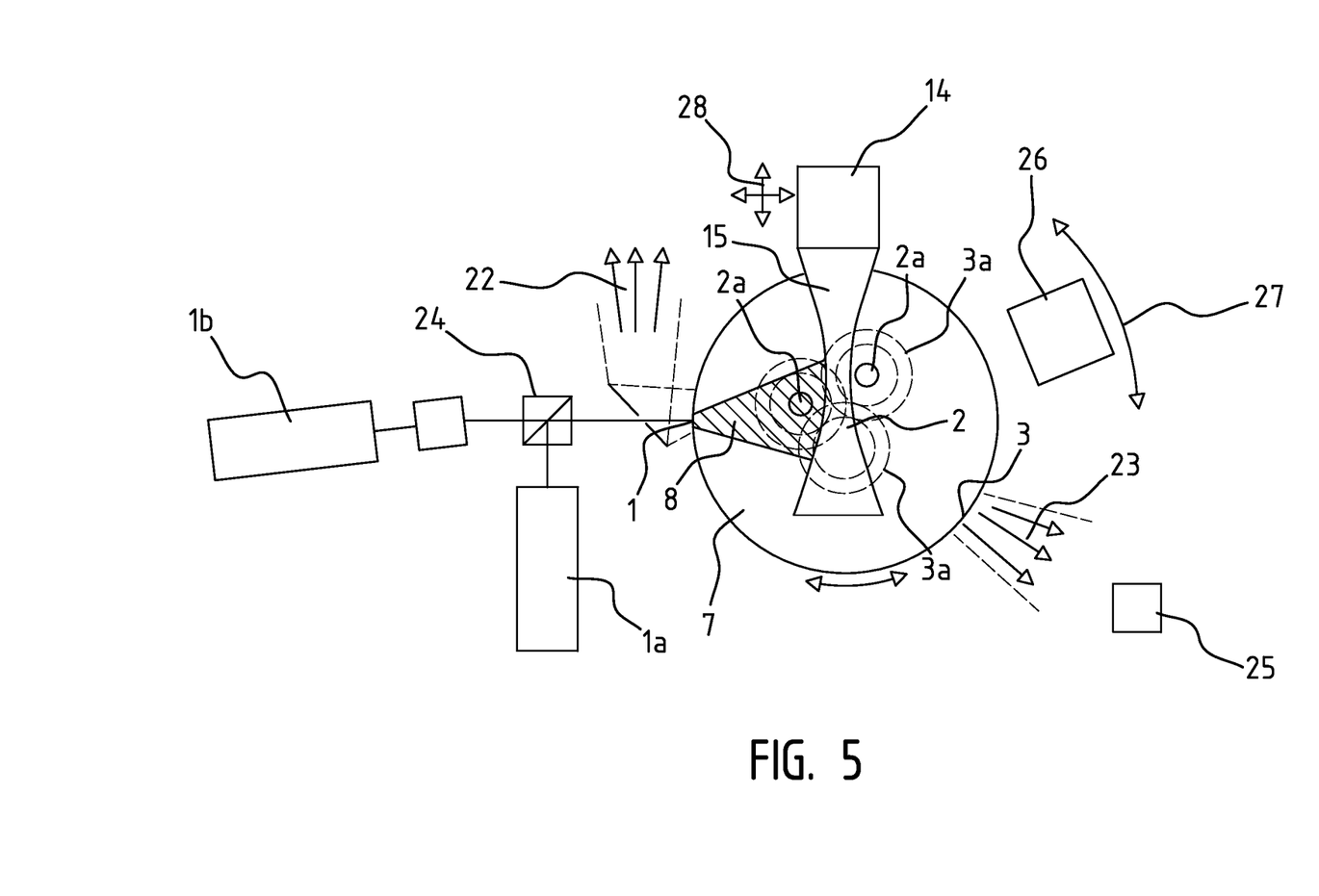
FIG. 5 represents a schematic view of a detection device according to an embodiment of the invention.

FIG. 5 represents a schematic view of a detection device according to an embodiment of the invention. In this device, a tissue 7 to be examined is irradiated with a first light source 1a and a second light source 1b. The first light source can be a short pulse, high intensity laser or modulated laser. This light source 1a is configured to generate the photo acoustic wave.

The second light source 1b can be a similar pulsed laser, though the pulses can be allowed to be longer. This light source 1b is providing the light for the deduction of the fluence in the defined volume element 2.

In FIG. 1, both light sources are combined in the light adder 24 and enter the tissue 7 at the same position 1. The light adder 24 can for instance be a grid or a half reflecting prism or a fibre-optic element.

The light entering the tissue is scattering as is represented by the shaded region 8. The portion of the light that enters the defined volume element 2, will be labelled by the acoustic focus 15, originating from the acoustic source 14. The labelled light can be measured by means of a light measurement element 25. This light measurement element 25 can be arranged at position 3, to measure the transmitted light 23 or at position 1, to measure the reflected light 22. Though the positions 2 and 3 are proposed for the light measuring element 25, other positions of the light measuring element 25 may be applied as well.

The sound generated by the photo-acoustic or opto-acoustic effect can be detected by the ultrasound measurement element 26. This element can be arranged as a single acoustic sensor, an array of acoustic sensors or a matrix of acoustic sensors. The position of the ultrasound measurement element can be varied as is indicated by arrow 27. In a similar way, the position of the acoustic source can be varied as well as is indicated by the arrows 28. Also the location of the position 1 relative to the tissue to be examined can be varied as is indicated by arrow 29. By thus varying the tissue relative to the device, a photo-acoustical excitation can be performed from position 1 as well as from position 3.

The invention is to be understood not to be limited to the exemplary embodiments shown in the figures and described in the specification. For instance in the description two light sources 1a and 1b are proposed. It might be possible to combine these two light sources into one light source. For instance where several pulses are used for the deduction of the fluence in the defined volume element and other pulses are used for the acousto-optic measurement.

In order to provide a well defined ultrasound focus 15, more interfering ultrasonic sources can be applied, with the same or with a different ultrasound frequency. For instance crossing beams of ultrasound can further provide a sharp focus.

In FIGS. 3 and 5, it is proposed to measure the light at positions 1 and/or 3. Other positions of the light measurement element 25 might be applied as well. For instance the element 25 can be arranged at a position in the close vicinity of position 1, as a near reflection mode measurement.

These and other modifications are considered to be variations that are part of the framework, the spirit and the scope of the invention outlined in the claims.

The invention claimed is:

1. A device, configured for measurement of specific photon absorption coefficient ($\mu_a$) in tissue based on combined photo-acoustic and acousto-optic measurements;
wherein the device comprises for photo-acoustic measurements:
a first light source configured for generating photons;
an ultrasound measurement element configured for measuring ultrasound originating from a defined volume element within the tissue and generated by light of the first light source that enters the defined volume element within the tissue;
wherein the device comprises for acousto-optic measurements:
a second light source configured for generating photons;
an ultrasound source, configured for generation of a defined sound wave pattern in the defined volume element within the tissue and configured for labelling light originating from the second light source that enters the defined volume element within the tissue; and
a light measurement element configured for measuring the amount of labelled light exiting the tissue;
wherein the device is provided with a processor, which is at least in communicative contact with the light measurement element and the ultrasound measurement element;
wherein the processor is configured to deduce from the amount of light generated by the second light source, and from the amount of labelled light originating from the defined volume element, an amount of light originating from the first light source actually entering the defined volume element; and
wherein the processor is further configured to deduce from the measured ultrasound generated in the defined volume element within the tissue by light originating from the first light source, and the amount of light from the first light source that actually entered the defined volume element within the tissue, the specific photon absorption coefficient ($\mu_a$) of the defined volume element within the tissue.

2. The device according to claim 1, wherein the light sources are lasers and are configured to dose the light in a pulsed or modulated way.

3. The device according to claim 1, wherein the second light source is configured to generate light of the same wave length as the light generated by the first light source.

4. The device according to claim 1, wherein the ultrasound source comprises a number of sound elements which are configured to provide a focus.

5. The device according to claim 4, wherein the number of sound elements are configured to provide crossing beams of sound waves.

6. The device according to claim 1, wherein the first light source is configured to be arranged on a first position and a second position relative to the tissue; and wherein the second light source is configured to be arranged on the first position, wherein the light measurement element is configured to be arranged substantially on the second position.

7. The device according to claim 1, wherein the first light source and the second light source are configured to be arranged on a first position relative to the tissue and wherein the light measurement element is configured to be arranged substantially on the first position as well.

8. The device according to claim 1, wherein the device is configured to scan through at least a portion of the tissue by measuring consecutive defined volume elements within the tissue, deducing the respective specific photon absorption coefficient ($\mu$) of each of the defined volume elements and wherein the device is further configured to generate from the thus generated data a graphic representation of the tissue, wherein different regions with different specific absorption coefficients ($\mu_a$) are configured to be visually determinable.

9. The device according to claim 1, wherein the light sources comprise arrays or matrices of individual sources.

10. The device according to claim 1, wherein the ultrasound source comprises arrays or matrices of individual sources.

11. The device according to claim 1, wherein the light measurement element comprises arrays or matrices of individual measuring sensors.

12. The device according to claim 1, wherein the ultrasound measurement element comprises arrays or matrices of individual measuring sensors.

13. A method for measurement of specific photon absorption coefficient in tissue, based on combined photo-acoustic and acousto-optic measurements;
wherein the method comprises for the photo-acoustic measurements:
radiating the tissue to be examined with a first light source;
measuring at the tissue surface an amount of sound generated within the tissue by a light of the first light source by the photo-acoustic effect;
calculating the amount of sound generated within a defined volume element from the measured amount of sound at the tissue surface;

wherein the method comprises for the acousto-optic measurements:
  generating a defined sound wave pattern in the defined volume element within the tissue to be examined;
  radiating the tissue to be examined with a second light source;
  labelling light originating from the second light source that enters the defined volume element by means of a defined sound wave pattern in the defined volume element;
  measuring an amount of labelled light exiting the tissue;
wherein the method further comprises:
  deducing an amount of light originating from the first light source that actually entered the defined volume element from the amount of light generated by the second light source and from the amount of labelled light originating from the defined volume element;
  deducing from the amount of light originating from the first light source that actually entered the defined volume element and the amount of sound generated in the defined volume element the specific photon absorption coefficient ($p_a$) of the defined volume element within the tissue.

14. The method according to claim 13, wherein a portion of the tissue to be examined is scanned through by consecutively shifting the defined volume element through the portion of the tissue and performing after each shift measurement steps in order to define in each volume element the specific photon absorption coefficient ($\mu_a$).

15. The method according to claim 14, wherein a two dimensional or a three dimensional graphical representation of the tissue is composed by graphically visualizing the specific absorption coefficient ($\mu_a$) in each volume element and placing the graphical visualization of each volume element in a two or a three dimensional location corresponding to the measured locations of the respective volume elements within the tissue to be examined.

16. The method according to claim 13, wherein specific photon absorption coefficients ($p_a$) can represent specific properties of the tissue in question.

* * * * *